United States Patent [19]

Fischell et al.

[11] 4,141,365
[45] Feb. 27, 1979

[54] EPIDURAL LEAD ELECTRODE AND INSERTION NEEDLE

[75] Inventors: Robert E. Fischell, Silver Spring; William R. Powell, Columbia, both of Md.

[73] Assignee: The Johns Hopkins University, Baltimore, Md.

[21] Appl. No.: 771,442

[22] Filed: Feb. 24, 1977

[51] Int. Cl.² .............................................. A61N 1/04
[52] U.S. Cl. .................................. 128/404; 128/347; 128/419 R
[58] Field of Search ............... 128/404, 408, 410, 411, 128/418, 419 P, 419 C, 419 E, 2.06 E, 2.1 E, 347

[56] References Cited

U.S. PATENT DOCUMENTS

| | | | |
|---|---|---|---|
| 3,367,339 | 2/1968 | Sessions | 128/418 |
| 3,416,534 | 12/1968 | Quinn | 128/418 |
| 3,572,344 | 3/1971 | Bolduc | 128/418 |
| 3,613,684 | 10/1971 | Sheridan | 128/347 |
| 3,620,219 | 11/1971 | Barker | 128/410 |
| 3,902,501 | 9/1975 | Citron et al. | 128/418 |
| 3,994,302 | 11/1976 | Brennen | 128/404 |
| 4,010,758 | 3/1977 | Rockland et al. | 128/418 |
| 4,026,301 | 5/1977 | Friedman et al. | 128/418 |

FOREIGN PATENT DOCUMENTS 283427 12/1970 U.S.S.R. ............................... 128/2.1 E

Primary Examiner—Lee S. Cohen
Attorney, Agent, or Firm—Robert E. Archibald; Samuel L. Sachs

[57] ABSTRACT

Tissue stimulation apparatus for positive positioning of an electrode-bearing lead proximous to tissue which is to be stimulated electrically, the invention particularly includes a body penetration and insertion assembly which carries an elongated flexible strip of physiologically inert plastic material having at least one electrode positioned thereon into contacting relation with said tissue. The insertion assembly comprises a hollow needle having a slot formed longitudinally along the length of one wall thereof, the slot allowing transverse removal of the flexible lead from the needle after proper positioning of the lead and after removal of the needle from the body. The present slotted assembly allows use of a flexible electrode lead having electrical connections at the external end thereof which are too large to pass through the hollow needle.

16 Claims, 11 Drawing Figures

EPIDURAL LEAD ELECTRODE AND INSERTION NEEDLE

BACKGROUND OF THE INVENTION

1. Field of the Invention

The invention relates to surgical apparatus and, more particularly, to an electrode lead and insertion assembly for positioning a tissue stimulating electrode in electrical contact with living tissue which is to be stimulated.

2. Brief Description of the Prior Art

Electrical stimulation of living tissue has previously produced beneficial therapeutic results ranging from stimulation of heart function to relief of severe pain states which are unresponsive to more conventional treatment. Implantable electrode leads have come into use which can be positioned in contact with tissue to be stimulated without the need for major surgery, the usually flexible electrode leads being carried by hollow rigid insertion needles which penetrate the skin and body wall to a suitable depth. The flexible electrode lead is then fed into a desired position relative to the tissue which is to be stimulated through the inserted needle, the needle then being withdrawn from the body over the entire length of the electrode lead while maintaining the lead in the desired position within the body. In such prior systems, the anterior end of the electrode lead could not be fitted with electrical connections or electrical components which could not be drawn through the hollow needle. In prior practice, it is therefore necessary for the surgeon to attach or form electrical connections to the electrode lead after the needle is pulled from the anterior end of the lead. Such connections, made under operating room conditions by medical personnel, are time consuming and often not comparable to the quality of electrical connections made under more controlled manufacturing conditions. The invention thus provides, among other things, the capability of implanting an electrode lead through the skin, which lead has electrical connections at its anterior end which are too large to pass through surgical insertion needles. Electrode leads which are pre-fabricated and/or connected to electrostimulation devices prior to implantation can therefore be conveniently used with substantial savings of time and with greater reliability than has previously been possible.

SUMMARY OF THE INVENTION

The present invention provides an electrode-bearing lead assembly which is capable of rapid penetration of the skin and body wall enclosing the tissue which is to be stimulated without the need for multiple incisions. The present assembly effectively carries an extremely flexible conductive lead into contact with the tissue, following which certain elements thereof are removed leaving the electrode lead in contact with the tissue. The flexible electrode lead than allows free movement of the body and of the stimulated tissue while maintaining electrical contact therewith and without damaging the tissue. In particular, the present structure allows the use of a flexible electrode lead assembly which has electrical connections attached to its external, non-implanted end, which connections are too large to pass through a conventional insertion needle, such as a Tuohy needle. In order to accomplish this desirable function, the present structure is provided with a rigid, external sleeve-like needle which penetrates the skin and body wall, the flexible electrode lead being fed through the needle into contact with the selected tissue. The needle is provided with a longitudinal slot extending the full length thereof so that the flexible electrode lead can be removed transversely from the needle on removal of said needle from the body, electrical connections existing on the external end of the electrode lead being left intact during removal of the lead from the needle.

Although the present invention can be practiced with electrode leads of varying description, the lead itself is preferably formed of a flexible, physiologically inert material. The body of the lead also serves to encapsulate and thus insulate multistranded, helical electrically conductive wires which usually extend throughout the lead from a unipolar electrode or bipolar electrodes at the distal, or implanted, end thereof to the anterior or external end of the lead, which external end is connected to a source of electrical energy. The electrode lead is preferably formed with an oval or rectangular cross-section along its length, i.e., the body of the lead is "flattened" in order to prevent rotation when placed into contact with tissue to be stimulated. When the present electrode lead is used to stimulate spinal cord tissue, the flattened conformation of the present lead also enables a better fit within the epidural space. The electrode lead can further be configured at the inner end thereof with a rounded tip which slopes from the upper surface of the lead to cause the lead to more naturally follow a desired path on insertion of the lead into an operative position, such as within the spinal column.

Accordingly, it is an object of the invention to provide an electrode lead assembly for insertion of an electrode-bearing flexible lead into the body and positioning therein with a minimum of surgical invasion.

It is a further object of the invention to provide an electrode lead assembly capable of implanting at least one end of a flexible, electrode-bearing lead into contact with tissue to be electrically stimulated, following which certain elements thereof can be removed leaving the implanted portion of the assembly in contact with said tissue, the elements of the assembly removed from the body being transversely withdrawn from the lead.

It is another object of the invention to provide an electrode lead assembly wherein a hollow, rigid body-penetrating portion thereof, through which a flexible, electrode-bearing lead is fed into the body, is formed with a longitudinal slot along its length to allow removal of the lead from said portion in a direction transverse to the longitudinal axis of the lead, thereby to allow leads having large electrical connections on the external ends thereof to be removed from said portion without disconnection of reforming of said electrical connections.

It is yet another object of the invention to provide an electrode lead assembly wherein a flexible lead has a shaped inner end portion to facilitate positioning of the lead in a desired relation to tissue which is to be electrically stimulated.

Further objects and advantages of the invention will become apparent in light of the following description of the preferred embodiments of the invention.

BRIEF DESCRIPTION OF THE DRAWINGS

FIG. 3b is a perspective of the additional ancillary apparatus of FIG. 3a;

DESCRIPTION OF THE PREFERRED EMBODIMENTS

While the invention relates to apparatus for inserting an insulated electrically conductive lead and electrode structure through a body wall and into contact with living tissue which is to be electrically stimulated, the following description particularly relates the use of the invention to stimulation of the spinal cord, particularly the lumber region thereof, such as is practiced in the relief of chronic intractable pain. Certain features of the invention particularly apply to this therapeutic procedure while other features of the invention can be more generally applied. Thus, even though the use of the invention is described hereinafter for a particular application, it is to be understood that such description is for the purpose of illustration only and does not limit the application and scope of the invention.

Figure 1A:
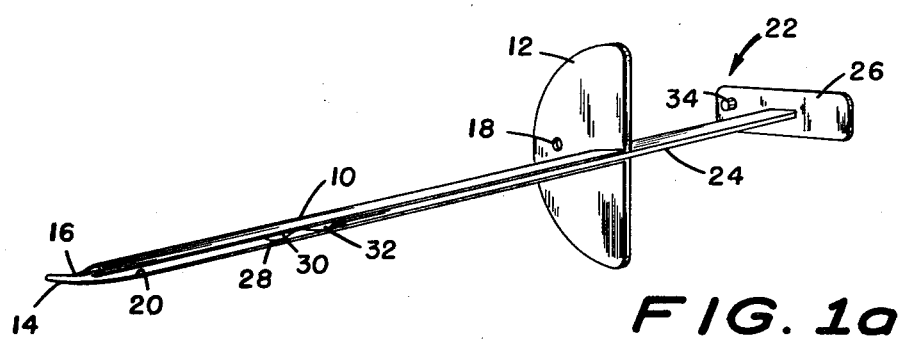
FIG. 1a is a perspective of the penetration and insertion portion of the present invention showing particularly the longitudinal slot formed in the side wall thereof and ancillary apparatus used therewith to first penetrate tissue.

Referring now to the drawings and in particular to FIG. 1a, the present electrode lead and insertion assembly can be understood to comprise a tubular insertion sleeve 10 having an enlarged, essentially semi-circular head 12 disposed on the outer end thereof. The inner end of the sleeve 10 is seen to be formed into a sharpened oblique point 14. The point 14 may curve slightly from the longitudinal axis of the sleeve 10 in order to facilitate useage thereof for particular applications such as will be described hereinafter. The point 14 may further be formed with an opening 16 disposed in the upper surface of the sleeve 10 as seen in FIG. 1a, the opening 16 being formed in that surface of the sleeve 10 toward which the point 14 curves. The enlarged head 12 has an aperture 18 formed therein which has its longitudinal axis disposed parallel to the longitudinal axis of the sleeve 10, the aperture 18 being spaced from the juncture of the sleeve 10 and the head 12 and can be conveniently aligned with said sleeve along a radius of the head 12 which is perpendicular to the straight side of said head. The sleeve 10 and head 12, which can conveniently be integrally formed of a material such as stainless steel, are essentially similar to a known surgical tool usually referred to as a Tuohy needle. The head 12 is grasped by a surgeon and used to apply pressure to the skin and underlying tissues of an animal, such as *Homo sapiens*, through the sleeve 10, the sleeve 10 being sufficiently rigid and the point 14 sufficiently sharp to enable penetration thereof through the skin and tissues.

The sleeve 10 differs markedly from prior surgical instruments in that a longitudinal slot 20 is formed in a side wall of the sleeve 10 and extends along the full length thereof. The slot 20 essentially lies in the plane defined by the straight line formed by the straight side of the head 12 and the line intersecting the juncture of the sleeve 10 and head 12 and which is parallel to the longitudinal axis of said sleeve. Thus, the opening provided by the slot 20 is transverse to the body of the sleeve 10 and "faces" to one side thereof. The sleeve 10 is preferably formed with an oblong cross-section, i.e., flattened on opposing surfaces relative to circular, along its length, such cross-section particularly allowing the accommodation of a flattened electrode lead within the lumen, i.e., the hollow interior channel, defined by said sleeve. While the sectional conformation of the sleeve 10 as shown and described herein is preferable in most applications, it is to be understood that differing sleeve cross-sections could be provided for accommodation of electrode leads of varying conformation.

Figure 1B:
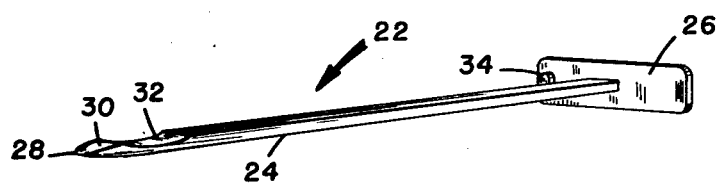
FIG 1b is a perspective of the ancillary apparatus of FIG. 1.

As will be appreciated relative to the ensuing description referenced both to FIGS. 1a and 1b, a stylet 22 is seen to be insertable into the sleeve 10 from the outer end thereof, the stylet 22 comprising a solid needle 24 and an enlarged head 26 formed on the outer end of said needle. The needle 24 has a cross-section which is similar in geometric contour to the cross-section of the sleeve 10, the needle 24 being dimensionally smaller than the interior channel defined by the sleeve 10 so that said needle 24 can be inserted into said sleeve to cause substantially all of the volumetric space within the sleeve to be occupied by said needle. Since the stylet 22 is seen to be partially inserted into the sleeve 10 in FIG. 1a, it is not possible to fully observe the shape of the inner end of the stylet. Although not a major feature of the invention, the inner end of the needle 24 as seen in FIG. 1b is preferably formed with a curve which is essentially congruent with the curve of the point 14 of the sleeve 10 as described hereinabove. The inner end of the needle 24 is also preferably formed with a sharpened, essentially rounded point 28 which is contiguous to a flat surface 30 lying immediately to the rear of the point 28. The plane of the surface 30 lies essentially parallel to the plane of the flattened upper surface of the sleeve 10, the surface 30 being of sufficient dimensional size to occupy the opening 16 in the point 14 of said sleeve. The inner end of the assembly, when the stylet 22 is fully inserted into the sleeve 10, thereby presents an essentially smooth surface without jagged contours which could act to tear tissue in an undesired fashion. The inner end of the needle 24 may further be formed with a depression 32 immediately to the rear of and contiguous to the surface 30, the depression 32 allowing said needle to bend more readily as needed to conform to the contours of the sleeve 10. The head 26 of the stylet 22 can conveniently be formed of a flat, rectangular plate having a pin 34 extending from the inner face thereof, the pin 34 aligning with the aperture 18 formed in the head 12 to provide a more positive connection therebetween when the stylet 22 is fully inserted into the sleeve 10. That portion of the head 26 extending outwardly from contact with the head 12 takes the form of a flap which can be used to withdraw the stylet 22 from the sleeve 10. The purpose of the stylet 22, as will be more appreciated from the following description, is to prevent tissue and liquid matter from entering the interior of the sleeve 10 on insertion thereof into the body.

Figure 2:
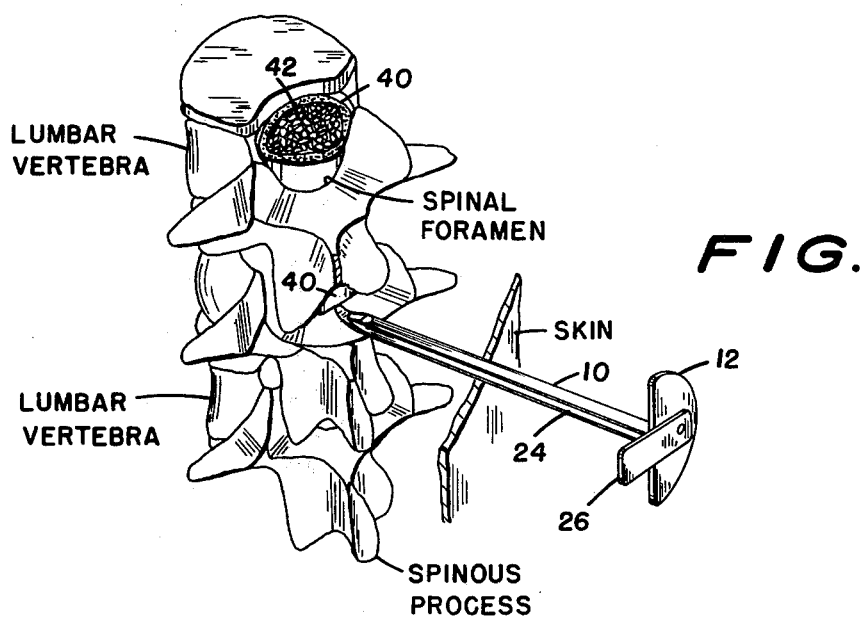
FIG. 2 is an idealized perspective of the assembly of FIG. 1 shown inserted into proximity to the spinal column.

Referring now to FIG. 2, the manner in which the apparatus of FIG. 1a is utilized in treatment of intractable pain in the human body can be seen. In treatment of the kind to be described hereinafter, electrical stimulation of tissue in the lumbar region of the spinal cord is effected by an electrode implanted in contact with or in proximity to the spinal cord. The implanted electrode is electrically connected by means of a flexible, conductive lead to a source of electrical energy which can be located either internally or externally of the body. The assembly of FIG. 1a, and particularly the sleeve 10, is used to implant the electrode and flexible head. As seen in FIG. 2, the stylet 22 is fully inserted into the sleeve 10, the assembly being then inserted into the body through a selected portion of the dorsal surface of the abdomen, the point 14 of the sleeve 10 entering the spinal foramen either between or to the side of the spinous processes on adjacent lumbar vertebrae. The head 12 and the head 26 on the stylet 22 are used to apply force to the sleeve 10 to cause penetration of the skin and tissue overlying the spinal column. The upwardly curved point 14 of the sleeve 10 better enables the sleeve to be positioned such that an electrode-bearing electrical lead assembly to be described hereinafter can be more readily located in a desired position. The stylet 22 serves inter alia to prevent tissue from entering the volumetric space within the sleeve 10 on insertion of the sleeve into the body. When the sleeve 10 is located in the substantially correct position, i.e., with the tip 14 positioned externally of and adjacent to the dura 42 as will be fully described hereinafter, the stylet 22 is fully withdrawn from the sleeve 10.

Figure 3A:
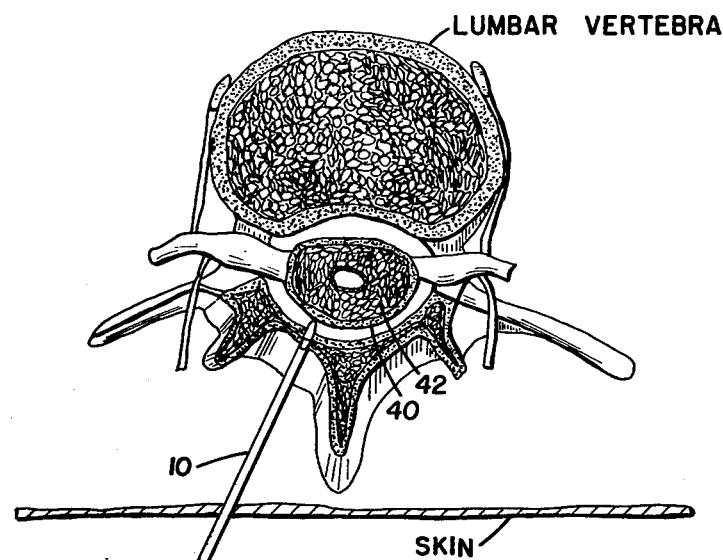
FIG. 3a is a cross-section taken through the lumbar region of the spinal column illustrating the positioning of the insertion portion of the present invention relative to the spinal column, an additional ancillary apparatus being shown in operative relation to the insertion portion.
Figure 3B:
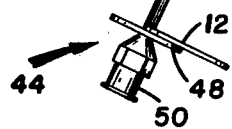

Referring now to FIGS. 3a and 3b the manner in which the tip 14 of the sleeve 10 is positioned within the spinal foramen of the spinal column is illustrated. Viewing the spinal column in section between two lumbar vertebrae, the dura 40 is seen to surround the spinal cord 42. The tip 14 of the sleeve 10 is positioned by "feel" near the outer surface of the dura 40 prior to removal of the stylet 22. When the stylet 22 is removed from the sleeve 10, a hollow needle 44 is inserted into the sleeve 10 to enable exact positioning of the tip 14 of the sleeve relative to the dura 40. As best seen in FIG. 3b, the needle 44 is formed with a hollow body member 46 having a cross-section congruent with the cross-section of the sleeve 10, the member 46 fitting substantially flushly within the sleeve 10. At the outer end of the body member 46, the needle 44 is fitted with a circular stop plate 48 which is surmounted by an open-ended cup 50, the lumen within the body member 46 extending into and communicating with the volumetric space defined by the cup 50. On full insertion of the needle 44 into the sleeve 10, the stop plate 48 abuts the outer surface of the head 12, thereby properly positioning the open inner end of the needle 44 at the open surface 30 of the sleeve 10. Physiological saline solution is then introduced into the cup 50 of the needle 44 and the entire lumen of the needle 44 is filled with the saline solution. The cup 50 is also filled with the saline solution sufficiently to form a meniscus therein which is visible at the open end thereof. The sleeve 10 with the needle 44 inserted thereinto can then be moved relative to the dura 40 to create a "potential space" between the dura 40 and surrounding tissues at the point where the tip 14 of the sleeve 10 contacts the outer surface of the dura. The manner in which the meniscus of the saline solution in the cup 50 responds to inward movement of the sleeve 10 enables the tip 14 of said sleeve to be accurately positioned in a desired location relative to the dura. If the dura 40 is inadvertently penetrated by the tip 14 of the sleeve 10, cerebral spinal fluid will move through the body member 46 of the needle 44 and into the cup 50, thereby signalling the user of the apparatus that the sleeve 10 has been inserted too deeply into the spinal foramen. When the tip 14 of the sleeve 10 is properly positioned, the needle 44 is removed.

Figure 4:
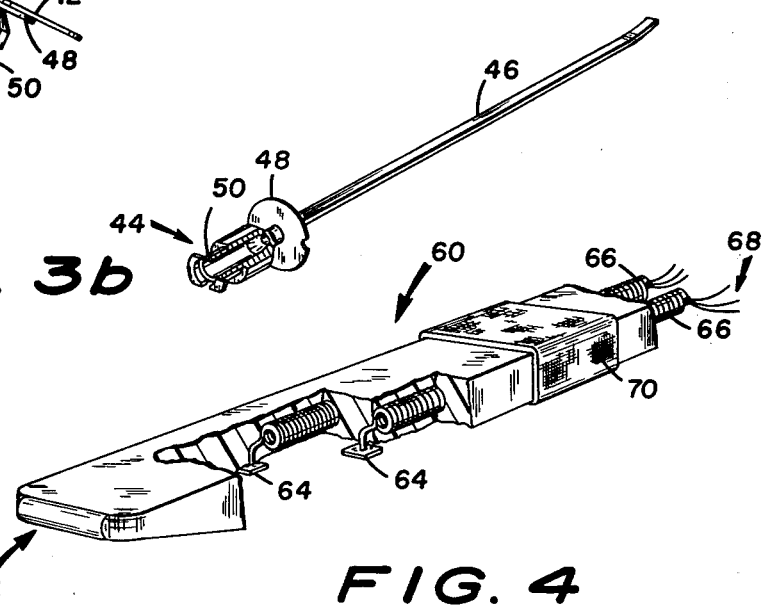
FIG. 4 is an idealized perspective of a flexible, electrode-bearing lead which is positioned in contact with the spinal column according to the invention.
Figure 5:
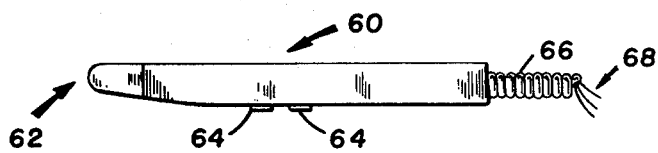
FIG. 5 is an elevation of the inner end of the lead of FIG. 4.

Prior to discussion of the actual insertion of an electrode-bearing, flexible lead into the spinal foramen, a description of a preferred lead assembly follows. Referring particularly to FIGS. 4 and 5, the inner end portion of a flexible lead 60 is seen to be generally oblong or oval in cross-section, i.e., the lead 60 has a flattened body portion formed of a flexible, electrically insulative, and physiologically inert material such as the plastic materials now being used for similar structures. The lead 60 could alternatively be of a rectangular cross-section or other oblong section capable of providing the functions described herein. For certain applications, the lead 60 could also be circular or semi-circular in cross-section, the sleeve 10 being formed to accommodate the lead 60. Corners of the tip 62 of the lead 60 are seen to be generally rounded transversely, the tip 62 sloping on the underside thereof along the longitudinal axis of the lead. This sloped tip 62, which is shaped substantially like the front end "running" portion of a sled, enables the lead 60 to deflect in a desired direction along the dura 40 when brought into contact therewith as will be more fully described hereinafter. The lead 60 has electrodes 64 disposed on the lower surface thereof, the electrodes 64 each being electrically connected by means of helical wires 66 to a source of electrical stimulation energy (not shown). The wires 66 each consist of multiple, redundant strands 68 of an electrically conductive wire material such as is well-known in the art. Each strand 68 is capable of providing a current flow adequate to maintain a desired level of electrical output from the electrodes 64. Thus, if fatigue failure or other factors cause breakage of one or more of the strands 68, the electrical stimulation system will remain capable of functioning as long as one of the strands remains intact in each of the wires 66. The helical nature of the wires 66 also allows substantial elongation and bending without breakage of the strands 68. The wires 66 are essentially encapsulated within the body of the flexible lead 60 to electrically insulate said wires. The electrodes 64 are both fixed in position on one face, i.e., the "lower" surface, of the lead 60, the relative spacing and position of the electrodes 64 being incapable of changing after implantation of the inner end of the lead 60. In addition, the disposition of both electrodes 64 on the surface of the lead 60 which is to face the dura 40 (as will be described in more detail hereinafter) enables the greater portion of the electrical stimulation energy applied through the electrodes to be directed into the spinal cord rather than be dispersed through surrounding tissue and bone. The lead 60 is made with flat upper and lower surfaces, i.e., in the aforementioned substantially oval sectional conformation, in order that the lead 60 can fit more efficiently and effectively within the epidural space, i.e., the potential space previously mentioned. The flat upper and lower surfaces of the lead 60 also act to prevent rotation of the lead about its own longitudinal axis after implantation within the epidural space. The lead 60 can further be provided with a mesh sleeve 70 which is slidable over the lead 60. The sleeve 70 can be formed of Dacron, a product of E. I. duPont Corporation, or other physiologically inert material formed into a mesh. The sleeve 70 can be positioned along the lead 60 internally of the body in proximity to the entry point of the lead in the spinal column, medical silastic being used to fix the sleeve 70 to the lead at that point. Tissue growing into the mesh of the sleeve 70 anchors the lead 60 into place. Although the lead 60 is described as having a bipolar electrode arrangement, it is to be understood that a unipolar electrode arrangement could be provided on the lead 60.

Figure 6:
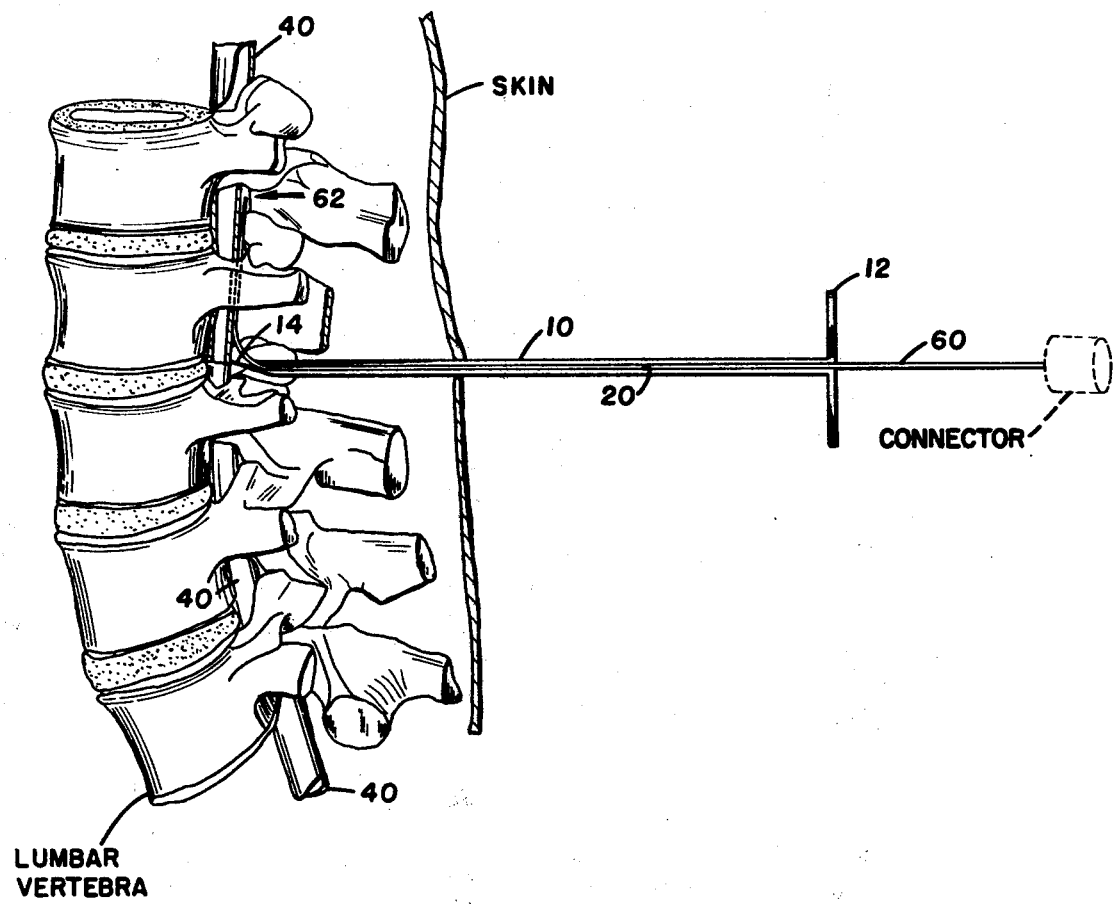
FIG. 6 is an idealized elevation illustrating the positioning of the lead of FIG. 4 into contacting relation with the spinal column.

Referring now to FIG. 6, it can be seen that the lead 60 is insertable into the sleeve 10, which sleeve has been inserted in a desired relation to the dura 40 as described hereinabove. The dimensions of the lead 60 are such that said lead can be inserted through the sleeve 10 without binding of the flexible material forming the lead and without damage to the electrodes 64. The lead 60 may optionally be provided with a stiffening member (not shown), such as a wire or the like, disposed longitudinally thereof to facilitate insertion of the lead into the sleeve 10 and subsequent removal of the sleeve from the lead. The lead 60 is inserted into the sleeve 10 with the electrode-bearing surface facing downwardly relative to the body of the individual into which the lead is being implanted. When the tip 62 of the lead 60 exits the tip 14 of the sleeve 10, the sloped underside of the tip 62 deflects against the dura 40 and is directed upwardly along the outer surface of the dura. The electrodes 64 are thus brought into contact with the dura 40 and face the spinal cord. The lead 60 is connected through the wires 66 to a source of electrical energy during this procedure in order that the lead can be positioned along the spinal cord at a location best suited for relief of the pain condition against which electrical stimulation is to be applied. The individual undergoing the procedure is conscious during the procedure and indicates subjective sensations produced by varying positions of the lead 60 along the spinal cord, the positon of the lead 60 being controlled from the outer end of the sleeve 10 by "feeding" of the lead through the sleeve.

Figure 7:
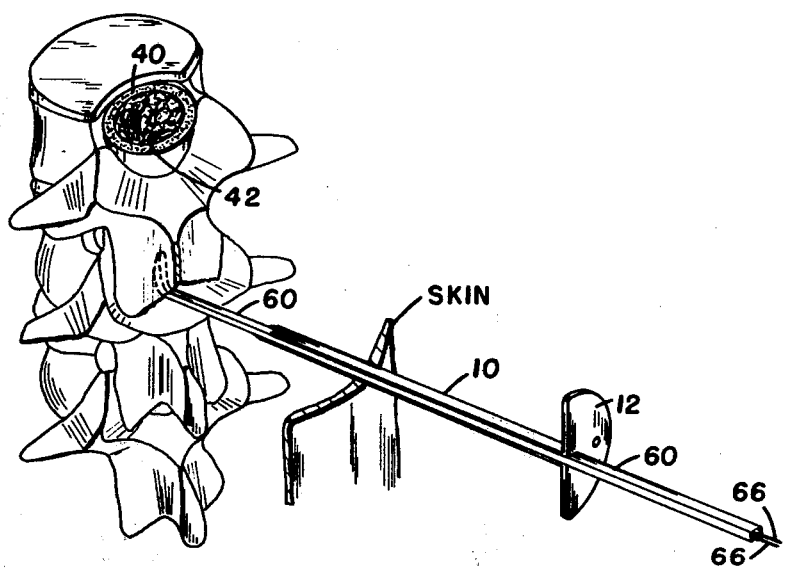
FIG. 7 is an idealized perspective illustrating withdrawal of the insertion portion of the invention from the body.
Figure 8:
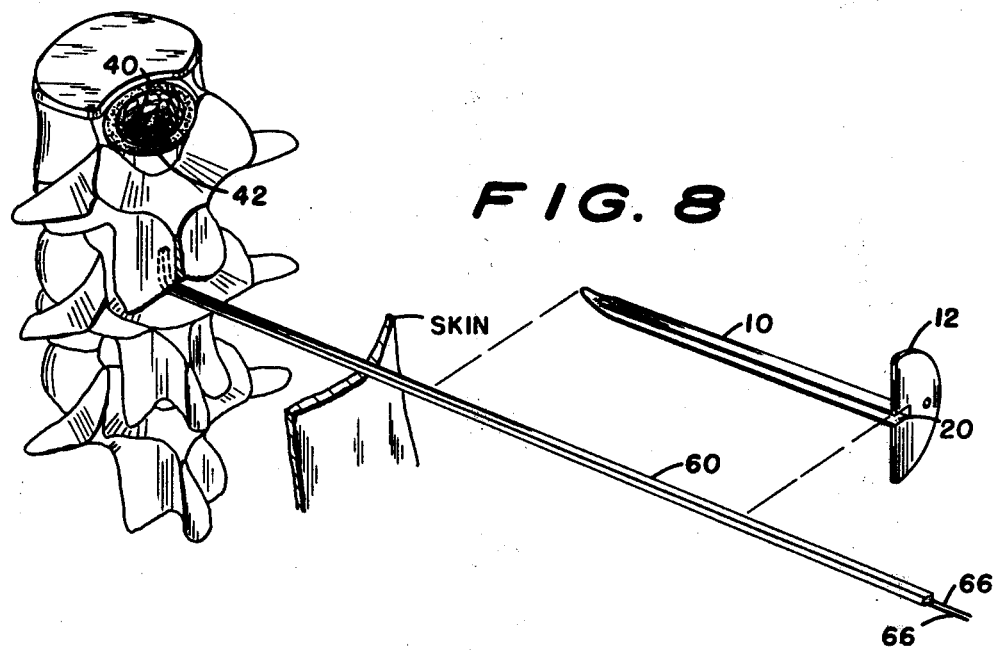
FIG. 8 is an idealized perspective illustrating the transverse removal of the insertion portion of the invention from the flexible lead after withdrawal of said insertion portion from the body; and, FIG. 9 is a perspective of an end member which can alternatively be disposed on a second embodiment of the insertion portion of the invention to facilitate handling thereof.

When the lead 60 is most advantageously positioned relative to the spinal cord, the sleeve 10 is withdrawn from the body along the lead 60 as seen in FIG. 7, the head 12 being used to pull the sleeve 10 from the body. In prior art electrode lead implantation procedures, the implantation needle corresponding to the sleeve 10 must be pulled along the full length of the lead and over the outer end thereof, thereby requiring the use of electrical connectors on the outer end of the lead which are small enough to fit within the lumen of the prior art insertion needle. Electrical connection to the external electrical source also must be disconnected to allow removal of the insertion needle from the lead. With the present invention as seen in FIG. 8, the body of the lead 60 can be removed from the sleeve 10 in a direction transverse to the longitudinal axes of the lead and sleeve through the slot 20 formed in the side wall of said sleeve. The use of electrical connectors on the outer end of the lead 60 which are larger than the inner dimensions of the sleeve 10 is therefore possible. Prefabricated sterile leads can be manufactured for implantation with the present invention which will reduce the complexity and temporal length of the implantation procedure. Prefabricated leads which are manufactured with permanent electrical connections to electrical pulse-producing apparatus is also now made possible by the present invention.

Figure 9:
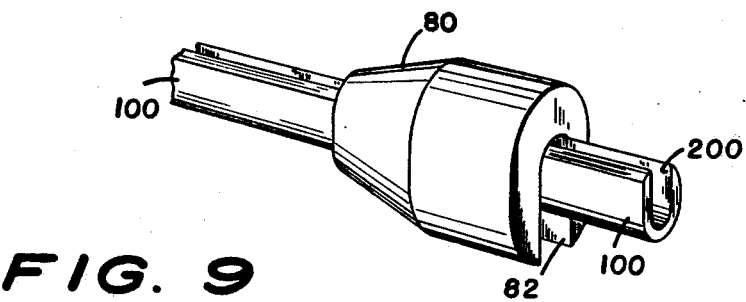

Referring now to FIG. 9, a sleeve 100 is an alternate embodiment thereof can be seen to have an enlarged end member 80 slidably received on the outer end thereof, the sleeve 100 not having fixed structure such as the head 12 formed thereon. The end member 80 is slotted along its length, the dimension of the slot 82 being sufficiently large to allow the lead 60 but not the sleeve 100 to pass therethrough. Therefore, the end member 80 can be utilized in the manner of the head 12 of FIG. 1 inter alia to insert the sleeve 100 into the body and to remove said sleeve from the body The end member 80 can be slidably removed over the outer end of the sleeve 100, the lead 60 then being transversely removed from the end member through the slot 82. The lead 60 is then removed from the sleeve 100 through the slot 200 in a manner similar to that previously described. As seen in FIG. 9, the slot 82 is formed in the end member 80 on the side thereof opposite the slot 200 in the sleeve 100. The end member 80 thus serves to maintain the structural integrity of the sleeve 100 while preventing the lead 60 from inadvertently slipping through the slot 200.

While the invention has been described relative to useage as means for implantation of an electrode-bearing lead in the body and for electrical stimulation of a portion of the spinal cord for relief of intractable pain, it is to be understood that the present assembly finds utility for other therapeutic application not explicitly described herein. Further, modification of the invention can be made in light of the teachings provided hereinabove. For example, the present structure can alternatively include a slotted sleeve which extends between the outer end of the sleeve 10 and the opening 16 or any portion of such distance, the slotted sleeve being essentially concentric with the sleeve 10 to retain the lead 60 within the sleeve 10 on insertion of the assembly into the body. This slotted sleeve could then be removed from the sleeve 10 in the same manner as the sleeve 10 is removed from the lead 60 or in the manner that the member 80 is removed from the sleeve 100. The head 12 could be retained on the sleeve 10 with use of such an outer slotted sleeve. Accordingly, in light of the foregoing, the invention is to be limited in scope only by the recitations of the appended claims.

What is claimed is:

1. Apparatus for effecting electrical contact between tissue internal of a living body and a source of electrical stimulation energy, comprising:

rigid sleeve means, forming a longitudinally disposed lumen, for penetrating tissues of said living body to position said apparatus in proximity to selected internal tissue, said sleeve means having a longitudinal slot disposed therein and extending along the length thereof, said slot being in communication with said lumen:

flexible electrically conductive lead means dimensioned so as to be longitudinally slidable through said lumen formed by said sleeve means, said lead means including an elongated body portion formed of a flexible physiologically inert dielectric material, said body portion being substantially oblong in cross-section and having flattened upper and lower surface portions; and electrode means electrically connected to and carried on a first end of said lead means and adapted to be connected electrically through said lead means to the source of electrical stimulation energy, said electrode means being disposed on one of said flattened surface portions of said substantially oblong body portion.

2. The apparatus of claim 1 wherein said sleeve means and lead means are substantially oblong in cross-section, said lead means further comprising electrically conductive wire means disposed internally of said body portion for electrically connecting said electrode means to the source of electrical stimulation energy.

3. The apparatus of claim 2 wherein said wire means comprise multiple helical strands formed of electrically conductive material.

4. The apparatus of claim 1 wherein said electrode means comprise at least two electrodes, the electrodes being spaced a fixed distance apart.

5. The apparatus of claim 1 further comprising electrical connector means connected to the end of said lead means opposite said first end thereof, said electrical connector means for connecting said lead means to said source of electrical stimulation energy, said electrical connector means being of larger dimensions than said lumen thereby preventing passage of said electrical connector means through said lumen formed by said sleeve means.

6. The apparatus of claim 2 wherein said lead means at said first end thereof is formed with a sloping tip portion sloping from the upper flat surface portion of said body portion toward the lower flat surface portion thereof along the longitudinal axis of said body portion, said electrode means being disposed on said lower surface portion of said body portion.

7. The apparatus of claim 1 further comprising enlarged head means disposed on one end of said rigid sleeve means, said enlarged head means for facilitating the handling of said rigid sleeve means.

8. The apparatus of claim 7 wherein said head means is slidable along the length of said sleeve means and has a slot longitudinally formed therein, said slot being disposed in a wall of said head means and being aligned with and in communication with said slot disposed in said sleeve means, wherein, said slot disposed in said head means is dimensioned for receiving said sleeve means therein.

9. The apparatus of claim 1 wherein said longitudinal slot disposed in said rigid sleeve means extends along the full length thereof.

10. The apparatus of claim 9 further comprising an enlarged head member carried on one end of said sleeve means said sleeve means further having a sharpened tip portion at the other end thereof, said tip portion of said sleeve means curving away from the longitudinal axis of the major portion of said sleeve means.

11. The apparatus of claim 10 wherein said sleeve means is substantially oblong in cross-section and has upper and lower surface portions which are substantially planar and parallel to each other.

12. The apparatus of claim 10 wherein said curved tip portion of said sleeve means has an aperture opening into and in communication with said lumen formed by said sleeve means, the portions of said tip portion defining said aperture lying in a plane which is substantially parallel to said planar surface portions.

13. The apparatus of claim 12 further comprising stylet means for reception and being longitudinally slidable within said sleeve means, said stylet means having a needle-like body portion receivable within said lumen of said sleeve means, said body portion having a tip member which curves away from the longitudinal axis thereof in conformity with said curved tip portion of said sleeve means, said tip member having a planar surface portion which is adapted to extend into said aperture formed in said tip portion of said sleeve means, the plane of said planar surface portion being essentially coincident with the plane in which said aperture lies.

14. The apparatus of claim 13 wherein that portion of the tip member adjacent to the planar surface portion has a depression formed therein.

15. The apparatus of claim 10 wherein said head member is fixed to said one end of said sleeve means, said head member comprising a semi-circular flat plate having a notch formed therein which aligns with and opens into said lumen of said sleeve means.

16. The apparatus of claim 15 further comprising stylet means for reception and being longitudinally slidable within said sleeve means, said stylet means having a needle-like body portion receivable within said lumen of said sleeve means and an enlarged head portion on one end thereof adapted to be proximous to said head member on said sleeve means, said enlarged head portion comprising a flat plate having a pin extending therefrom, said semi-circular flat plate of said head member having a locating aperture disposed therein, said pin being aligned with and received within said locating aperture formed in said head member on full insertion of said stylet means into said sleeve means.

* * * * *